# United States Patent [19]

Barratt

[11] 4,254,8

[45] Mar. 10, 19

[54] FOLDABLE DISPOSABLE SHARPS CONTAINER

[76] Inventor: Don C. Barratt, 1255-3B Weathervane La., Akron, Ohio 44313

[21] Appl. No.: 971,305

[22] Filed: Dec. 20, 1978

[51] Int. Cl.³ .............................................. A61B 17/06
[52] U.S. Cl. ................................. 206/63.3; 206/380; 229/33; 229/36; 229/44 R; 229/45 R
[58] Field of Search ....................... 206/480, 83.3, 380, 206/382, 383; 229/33, 36, 44 R, 45 R

[56] References Cited

U.S. PATENT DOCUMENTS

| | | | |
|---|---|---|---|
| 2,110,572 | 3/1938 | Foote | 206/480 |
| 2,319,078 | 5/1943 | Ullman | 229/33 |
| 2,511,523 | 6/1950 | Abrams | 229/33 |
| 3,148,823 | 9/1964 | Diez | 229/33 X |
| 3,335,847 | 8/1967 | Murphy et al. | 206/380 |
| 3,944,069 | 3/1976 | Eldridge, Jr. | 206/( |
| 4,151,913 | 5/1979 | Freitag | 206/( |

FOREIGN PATENT DOCUMENTS

561841 11/1957 Belgium ...................................... 229

*Primary Examiner*—Joseph Man-Fu Moy
*Attorney, Agent, or Firm*—James F. Cottone

[57] ABSTRACT

A disposable container for used sharp surgical imp ments is formed of an outer casing lined with resili pads, and is configured to fold into the closed posit where it is retained via simple mechanical means wh permit reopening if necessary. The basic device cludes integral edge guards and a variety of clos retaining means, and includes an embodiment havin transparent outer casing to facilitate visual inspect and inventory of the surgical implements after contai closure prior to final disposal.

10 Claims, 10 Drawing Figures

FOLDABLE DISPOSABLE SHARPS CONTAINER

BACKGROUND OF THE INVENTION

1. Field of the Invention

The present invention relates to the field of special purpose disposable containers, and in particular to containers for use in the disposal of used medical/surgical sharp implements.

2. Description of the Prior Art

Sharp implements such as suture and hypodermic needles, expendable scalpel blades, and the like, are used regularly in all forms of surgical procedures. Following the surgical procedures, these items must be disposed of in a safe manner to assure that possible injury and infection of the operating room and other hospital personnel does not result. An additional consideration in the use of such sharp implements (hereinafter referred to alternately as "sharps") during surgery is the necessity of providing an accurate system for determining how many such implements were used, and to insure that all implements used have been accounted for following the surgical procedure. In the recent past, various sharps disposal and count devices and techniques have been proposed in response to these problems.

A recently proposed device for retaining and disposing of sharps during and after a surgical procedure is described in U.S. Pat. No. 4,076,882 to Fenster, et al. The device proposed by Fenster comprises a pressure sensitive adhesive coating (one time use) on a layer of polyurethane foam, all of which is carried by a scored cardboard backing which is folded closed after use to serve as the sharps disposal medium.

Similar sharps disposal devices employing, respectively, magnetic and adhesive layers on a foldable foam pad are described and illustrated in U.S. Pat. Nos. 3,727,658 and 3,944,069, both to J. D. Eldridge, Jr. Another system similar to the devices described in the previously cited patents, but also providing for a method for maintaining an accurate count of the number of sharp implements utilized during the surgical procedure, is illustrated and described in U.S. Pat. No. 4,008,802 to Freitag.

Also, U.S. Pat. No. 4,013,109 to Sandel describes a disposable container for surgical instruments which embodies a non-deformable casing having magnetic sheets covering the entire surfaces of both lower and upper portions of the case.

All of the disposable receivers described in the above cited patents suffer from a number of disadvantages. The two most significant of these disadvantages are—the inability of the operating room personnel to close and reopen (without damage to the container) the sharps disposal device at will, or as required during the surgical procedure; and the inability of the operating room personnel to make a visual examination of the contents of the disposable container after it has been closed or otherwise readied for disposal. For example, although U.S. Pat. No. 4,008,802 discloses a system for maintaining a count of the used sharp implements, this count cannot be verified after the pad has been folded upon itself and adhesively secured together.

In brief, the prior art disposable receiver disadvantages are: (a) most can be opened accidentally, as with magnetic or hook and loop (Velcro) closures; (b) others are rendered useless (permanently damaged) when reopened, as with adhesive closures; (c) rigid plastic receivers fracture easily and their closure means are highly susceptible to failure; and (d) most devices allow lateral side exposure of unsecured sharps. Each shortcoming outlined above precludes the desired degree of safe handling, safe disposal, or reopening and/or visual inspection for accountability of the used sharps.

Therefore, it is clear that a need exists for a system for the safe and economic disposal of sharps which eliminates the various disadvantages which have been experienced with previously proposed devices.

SUMMARY OF THE INVENTION

It is therefore a primary object of the present invention to provide an improved disposable receiver for retaining and disposing of sharps during and following a surgical procedure.

A further object of the present invention is to provide a foldable disposable receiver having sufficient features to overcome the combination of disadvantages of the prior art devices.

Another object of this invention is to provide a foldable disposable receiver comprised of readily available and low cost materials having edge guard means to preclude inadvertent exposure of the sharps along the edge of the device; and further having simple and positive means for retaining the foldable disposable receiver in the closed position while permitting reopening if required; and being capable of unobstructed see through construction permitting visual inspection of the contents of the receiver in its closed position.

In a preferred embodiment of the present invention the outer casing of the receiver is made from a transparent material to enable the operating room personnel to make a visual inspection of the sharp implements contained within the receiver after it has been closed and readied for disposal, and has straightforward die cut tuck-in tab/slot means for retaining the container in the closed position.

BRIEF DESCRIPTION OF THE DRAWINGS

Additional objects and advantages of the invention will become apparent to those skilled in the art as the description proceeds with reference to the accompanying drawings wherein.

DETAILED DESCRIPTION OF THE PREFERRED EMBODIMENTS

Figure 1:
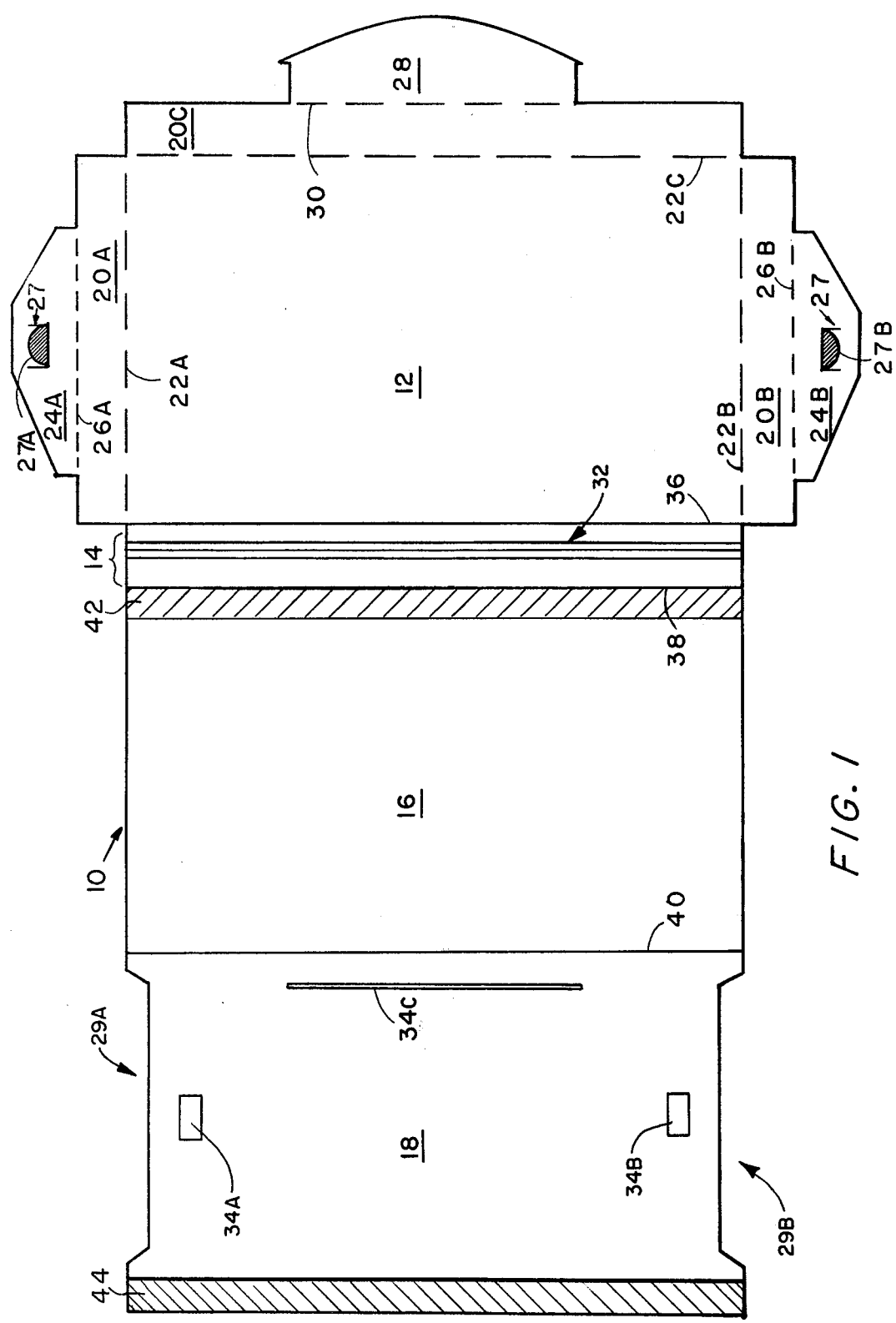
FIG. 1 is a plan view of a preferred embodiment of the foldable disposable sharps container according to the present invention.

Referring now to FIG. 1, there is shown a plan view of a preferred embodiment of the Foldable Disposable Sharps Container according to the present invention Foldable container 10 is shown in the unassembled condition as a unitary device comprised of a multi-portioned top section 12, an edge section 14, a bottom section 16, and a back section 18. These four elements comprise the outer casing of the foldable container 10 and may be fabricated from any of a number of well-known paperboard or plastic sheet materials. The top section 12 has edge guard portions 20A-20C disposed along three of its edges, which edge guards are foldably separated from the top section 12 by a plurality of fold lines 22A-22C. Edge guards 20A and 20B have restraining tab portions 24A and 24B, respectively appended to them, and are foldably separated therefrom by a pair of fold lines 26A and 26B. Suitably positioned on each of the restraining tabs 24A and 24B is a die cut/engaging means 27. The engaging means 27 are formed as a three sided cut having semicircular raised portions 27A and 27B centrally disposed within the cuts. A locking tab portion 28 is carried by the edge guard 20C, being foldably separated therefrom by a fold line 30. The edge guards 20A-20C, restraining tab 24A and 24B, and the locking tabs 28 are integrally formed with, and form portions of, the top section 12. This four element outer casing may be formed by die-cutting of the sheet materials, and the various fold lines may be formed by pressure scoring, or similar processes.

A plurality of closely spaced fold lines 32 are centrally positioned along the long dimension of edge section 14. These lines assist in the foldable closing action of the foldable container 10 by allowing the edge section 14 to serve as a variable width hinge section around which the top section 12 and the bottom section 16 may articulate. Three rectangular die cut apertures (hereinafter referred to as slots), 34A-34C are formed in the back section 18 wherein the alphabetic designations A and B coincide with the corresponding designations of engaging means 27A and 27B with which they mate when the foldable container 10 is in the closed position. The sides of back section 18, adjacent to the slots 34A and 34C, are broadly notched as shown in the regions 29A and 29B to facilitate this mating engagement. Similarly, the slot 34C mates with locking tab 28 when the container is in the closed position. A plurality of fold lines 36, 38 and 40 are positioned, respectively, between top section 12 and edge section 14; between edge section 14 and bottom section 16; and between bottom section 16 and back section 18.

Suitably disposed along a long edge of the bottom section 16 and the back section 18 are a pair of adhesive laminate regions 42 and 44. These regions may be implemented by any of the well-known means such as two-sided, pressure sensitive adhesive tapes with peelable coverings, cold or hot laminates, and the like. In use, the back section 18 is folded (along the fold line 40) onto the bottom section 16 such that the adhesive laminate regions 42 and 44 mate. The structure thus formed, in combination with the slots 34A-34C, provides sleeves or reception of the engaging means 27A and 27B, as well as the locking tab 28. A pair of foam pads 46 and 48 are secured to the top section 12 and the bottom section 16, respectively, as seen best in FIGS. 2 and 3. Alternately, a single piece foam pad (not shown) may be disposed over both the top section 12 and bottom section 16, or over any desired lesser areas of these sections. Both FIGS. 2 and 3 show the folding under of back section 18 onto bottom section 16, which places the locking slots 34A-34C in position for engagement with the engaging means 27A and 27B.

Figure 3:
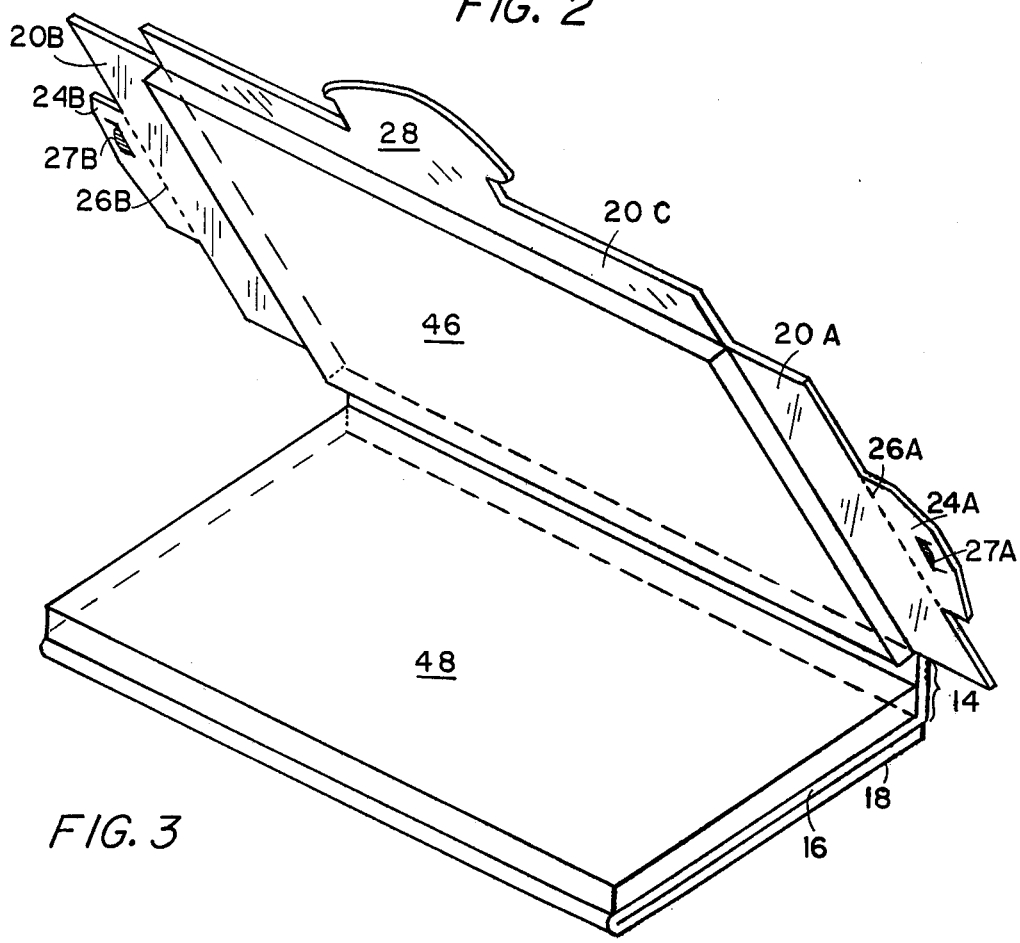
FIG. 3 is a perspective view of the foldable container of FIG. 2 shown in the assembled condition, partially closed.
Figure 4:
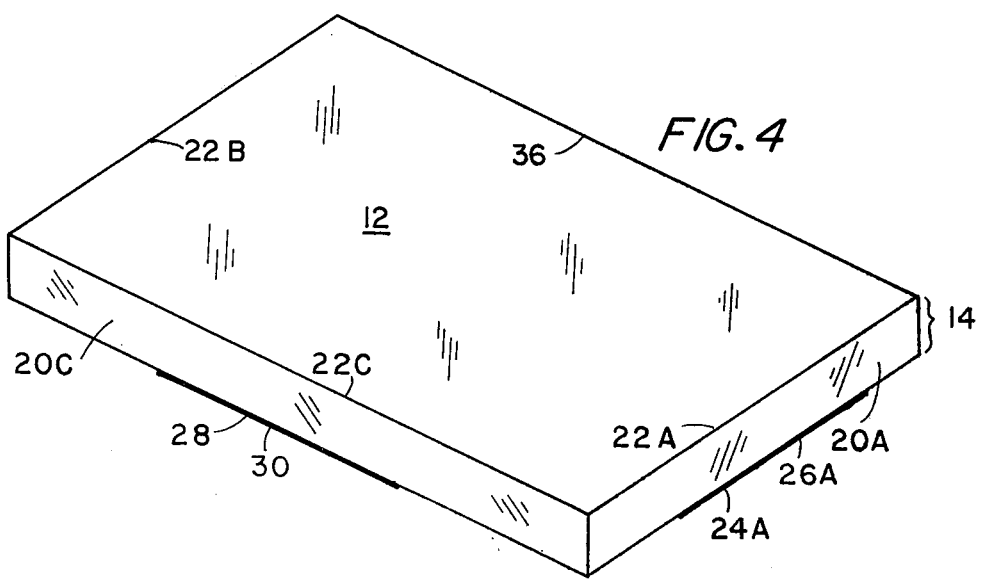
FIG. 4 is a perspective view of the foldable container of FIG. 1 in the closed condition, ready for disposal

In use, the foldable container 10 would be assembled into a first configuration (wallet-like as shown in FIG. 3) to serve as a receiver for the sharps to be retained, and would be folded closed into a second configuration (flat box-like as shown in FIG. 4) to serve as a container for the sharps to be disposed in.

Figure 2:
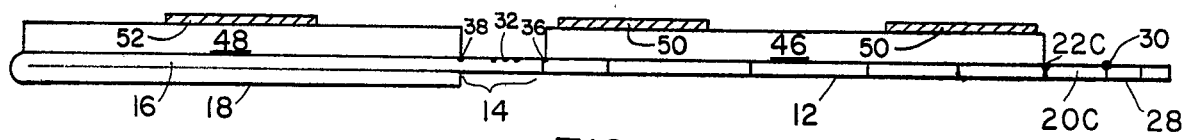
FIG. 2 is a side view of the foldable container showing the foam pads in place.

Referring now to FIG. 2, there is shown a side view of the foldable container 10 as it would be arranged for use. The back section 18 has been folded onto the bottom section 16 and held there by the mating adhesive regions 42 and 44 (not shown); the fold lines 30, 22C, 36 and 38 are shown (slightly exaggerated in size) in their appropriate locations; and both foam pads 46 and 48 are shown exposed to serve as resilient surfaces for reception of the used sharps. In use, the disposed sharps are hooked into the foam pads 46/48—ideally, the sharps would be stitched into (shallowly stuck into, then pushed out of) the foam pads 46/48—to preclude their subsequent moving. The upper surfaces of the foam pads 46 and 48 may be coated with adhesive or magnetic layers or stripes, to further prevent the deposited sharps from moving about. These layers have not been shown, but may be substantially similar to those illustrated in the aforementioned two U.S. Patents to Eldridge, Jr. In the case of adhesive layers, the adhesives may be applied to the foam pads in intermittent/cooperating patterns (ie., complementary patterns) so as to preclude the pads from sticking to themselves. That is, a stripe (or other pattern) of adhesive applied to the foam pad 46, in the form of regions 50, and to foam pad 48, in the form of regions 52, to retain the deposited sharps would mate with corresponding portions of the foam pads 46 and 48 that had not been so coated; and vice versa. Thus, both pads would retain deposited sharps, but would not be self-adhering. For simplicity, only a few (three) regions 50 and 52 have been shown; of course, a much larger number of intermittent/cooperating regions may be employed.

During the surgical procedure, the sharps may be placed on or hooked into the foam pads (and removed) as frequently as required, and at a suitable stage in the procedure, the foldable container 10 may be folded into the closed position as shown in FIG. 4. While the engaging means 27A and 27B and the locking tab 28 retain the foldable receiver 10 in the securely closed position, the receiver may be readily reopened without damage if required for sharps inventory or inspection, or for any other purpose. The two types of restraining means provide a hierarchy of locking capabilities. The engaging means 27A/27B and slots 34A/34B combination yield an intermediate level of closure retaining means. While the engagement of this combination is positive, it can be overcome by application of finger pressure on the semicircular raised portions of the engaging means 27A/27B. The locking tab 28 and slot 34C combination yields a final level of foldable receiver closure retaining. While the mating engagement of these items can be overcome by manual manipulation, somewhat more effort is required, and the mated position provides a good deal more positive action. The combination of these two levels of reopenable closure retaining means imparts a highly useful capability to the foldable container 10. While in the closed position, the sharps are securely held in place by being hooked into the foam pads 46/48; and further by the adhesive/magnetic means; and are further securely held in place by the compression action of the foam pads. The edge guards 20A-20C provide a further measure of protection during handling and disposing of the foldable container 10 by providing a barrier which positively prevents any sharp points or edges from being inadvertently contacted by the handling personnel.

Figure 5:
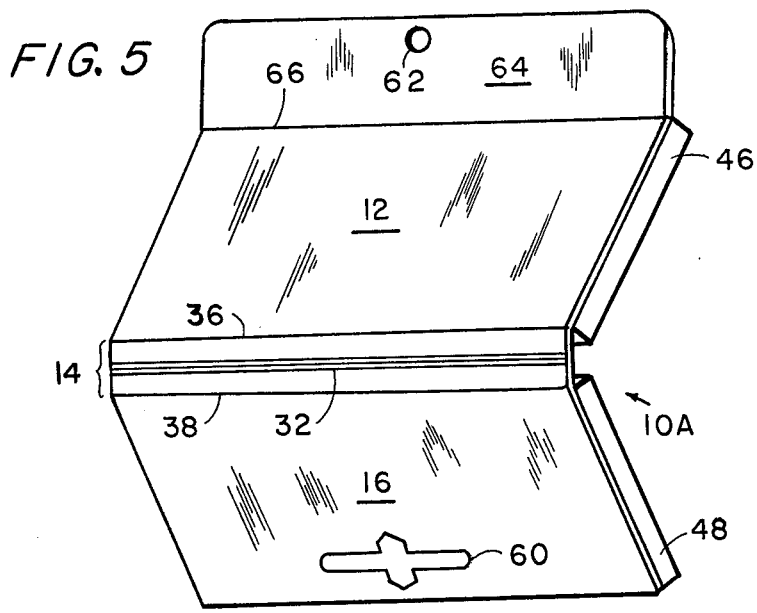
FIGS. 5-7 show alternate embodiments of the foldable container with emphasis on alternate restraining means.
Figure 6:
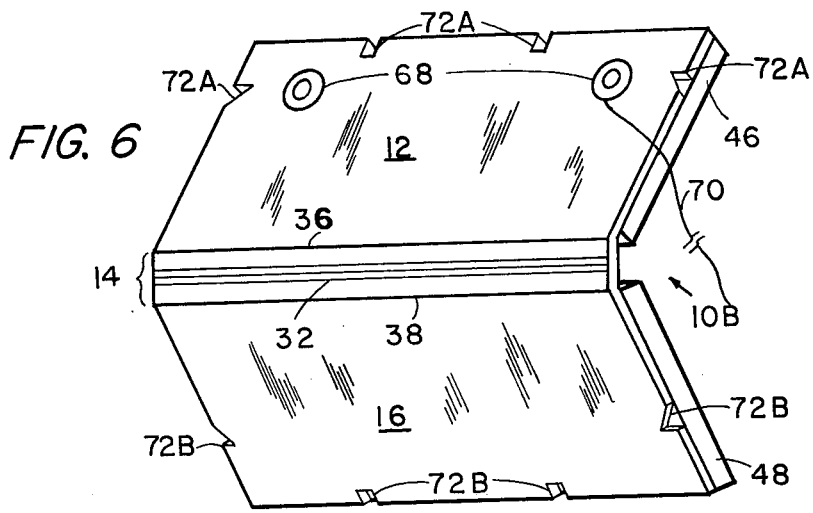
Figure 7:
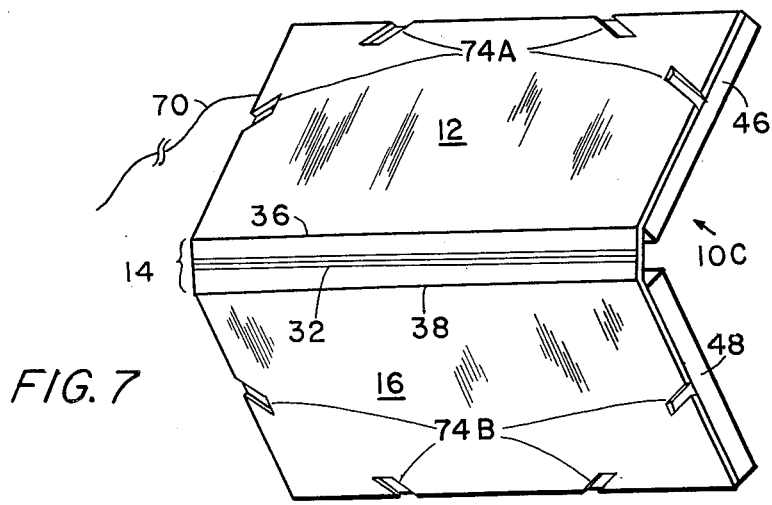

A number of alternate embodiments of the foldable container 10 are shown in FIGS. 5-7. Generally, these embodiments provide alternate retaining means and a simplified basic outer casing. All three embodiments shown are substantially identical to that of FIG. 1, the major differences being: (a) the deletion of the back section 18 and hence the adhesive regions 42 & 44; (b) the deletion of the restraining tabs 24A and 24B and locking tab 28; and (c) the addition of the various retaining means. For clarity of description, these three embodiments have been designated as foldable receivers 10A, 10B and 10C corresponding respectively to FIGS. 5, 6 and 7. These embodiments are comprised top sections 12 carrying foam pads 46, and bottom sections 16 carrying foam pads 48. As before, the foam pads 46/48 may be formed as a single element, or one or the other may be reduced in size, or deleted. The two casing sections are connected by the integrally formed edge sections 14, being partitioned therefrom by the fold lines 36 and 38. As before, the edge section 14 may carry the plurality of fold lines 32 to assist in the required hinging action.

Figure 5A:
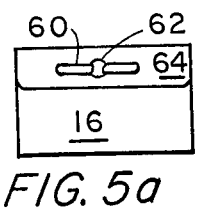
FIGS. 5a, 6a and 7a shows the detail description of the restraining means of FIG. 5, FIG. 6 and FIG. 7 respectively.

The embodiment of FIG. 5 employs a clasp fastening means to retain the foldable container 10A in the closed position. The fastening means is comprised of a two-pronged metal clasp 60 appropriately positioned on the bottom section 16, and a corresponding hole 62 formed in a flap portion 64. The flap portion 64 may be integrally formed with the top section 12 and is separated therefrom by a fold line 66. FIG. 5A shows the foldable container 10A in the closed position, ready for disposal. This embodiment is particularly amenable to fabrication from transparent casing materials to provide for visual inspection of the encased sharps after the container has been closed. This is due to the total absence of vision obstructing fastening means on the top section 12. To implement the see-through version of foldable container 10A, the casing (comprised of elements 12, 14, 16 and 64) is formed from a suitable one of the well-known transparent sheet materials, and the foam pad 46 is deleted from the device. Thus, any sharps deposited on the foam pad 48 are available for visual inspection, inventory, and the like, at any time.

Figure 6A:
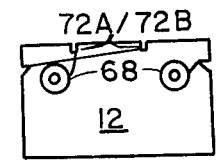

The embodiment of FIG. 6 employs a string-tie fastening means to retain the foldable container 10B in the closed position. The fastening means is comprised of: (a) a pair of round eyelet-type elements 68, one of which is fitted with a length of string 70; and (b) a plurality of appropriately located edge notches 72A and 72B formed into the peripheries of the top section 12 and the bottom section 16. As shown in FIG. 6A, the string 70 is fitted into mating edge notches 72A/72B while being wrapped around a folded, closed container, thereby securely retaining the foldable container 10B in the closed position, ready for disposal. The resilience of the foam pads in the vicinity of the side edge notches 72A and 72B, as they bear on the portions of the string, helps to maintain the string 70 under slight tension thus increasing the compression on the discarded sharps and preventing their shifting about. An additional measure of utility and safety can be incorporated into the configuration of FIG. 6 merely by including edge guards (not shown) similar to the type shown as elements 20A-20C in FIG. 1. The edge guards for foldable container 10B would be appended to either the top section 12 or t bottom section 16, and would contain suitable ad tional notches to cooperate with the described ed notches 72A/72B.

Figure 7A:
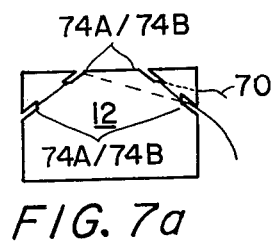

The embodiment of FIG. 7 shows a simplified versi of a foldable container 10C wherein only a length string 70 and a plurality of specially shaped ed notches 74A and 74B are employed to retain the devi in the closed position for disposal. The string 70 may firmly attached to the device by being placed betwe the foam pad 46 and the top section 16 and subjected the same adhesive means employed therebetween. T edge notches 74A and 74B are formed into the t section 12 and bottom section 16 at corresponding m ing locations as in FIG. 6, but are angled with respect the normal to the edges in which they are formed. T angling greatly aids in retaining the string 70 securely the edge notches 74A/74B. Also, as with the embo ment of FIG. 6, the foam pads 46 and 48 assist in kee ing the string 70 under additional tension. Howev friction of the edge notches 74A/74B against the stri 70, as well as the shape of the notches per se, provi the main mechanisms for holding the string 70 in t desired position. FIG. 7A shows the folded contain 10C in the closed position and indicates the preferr orientation of the edge notches 74A/74B.

The embodiments of FIGS. 6 and 7 have spec economic advantages due to their simple constructi and almost total absence of costly or complex retaini means. This lack of complexity in manufacture matched by its ease in use. As is apparent from t above description, no intricate user manipulation required; the retaining means are capable of being used many times; and good security of the dispos sharps is afforded by all embodiments.

Although the invention has been described in ter of selected preferred embodiments, the inventi should not be deemed limited thereto, since other e bodiments and modifications will readily occur to o skilled in the art. For example, while the embodiment FIG. 5 has been suggested as being ideal for a "s( through" device, it is clear that this approach could al be extended to the embodiments of FIGS. 6 and 7. Al: the depicted number and location of the various reta ing means—locking tabs/clasps/string-ties and so f( th—have been set forth merely as illustrative configu tions. It is therefore to be understood that the append claims are intended to cover all such modifications fall within the true spirit and scope of the invention.

What is claimed is:

1. A reopenable, disposable sharps container compi ing:

(a) an outer casing having a planar top section an( planar bottom section connected by a hinge s( tion;

(b) at least one of said planar sections being foldal connected to a back panel fitted upon said plaı section thereby converting said at least one plaı section into a flat pocketed planar section;

(c) at least one resilient pad attached to at least one said planar sections; and (d) at least two types of two-part retaining mea integrally formed into said planar sections for r penably retaining said container in a folded, clo: position via a hierarchy of retaining levels by engagement of a first protruding part of a first ty of retaining means having a first width connec to one of said planar section with a second ap tured part of a corresponding type of retaining means havng a width greater than said first width formed into said pocketed planar section to provide a first level of clsoure retaining, and by the engagement of a first protruding part of a second type of retaining means having a predetermined width connected to one of said planar sections with a second apertured part of a corresponding type of retaining means having a width substantially the same as said predetermined width formed into said pocketed planar section to provide a second level of closure retaining.

2. The reopenable, disposable sharps container of im 1 wherein said planar sections have inner and ter surfaces and said at least one resilient pad is attached to an inner surface of at least one planar section d said folded closed position corresponds to a configution wherein said planar sections of said outer casing ve said at least one resilient pad sandwiched therebeeen.

3. The reopenable, disposable sharps container of im 2 having one resilient pad attached to said inner face of said bottom section wherein said top section ransparent to permit visual inspection of said sharps ntained therein.

4. The reopenable disposable sharps container of im 2 having one resilient pad attached to an inner face of said top and bottom sections whereby said ntained sharps are retained under compressional ces.

5. The reopenable disposable sharps container of im 4 wherein said resilient pads have complementary hesive layers patterned thereon for adhesively retain-; deposited sharps but precluding the mutual adher-; of said pads in the absence of said deposited sharps.

6. A reopenable disposable sharps container compris-
;:
(a) an outer casing having a planar top section and or planar bottom section foldably interconnected by a hinge section;
(b) at least one of said planar sections being foldably connected to a back panel fitted upon said planar section thereby converting said at least one planar section into a flat pocketed planar section;
(c) at least one resilient pad attached to at least one of said planar sections:
(d) planar edge guard means carried by at least one of said planar sections;
(e) at least two type of two part retaining means integrally formed into said planar sections for reopenably retaining said container in a folded, closed position via a hierarchy of retaining levels by the engagement of a first protruding part of a first type of retaining means having a first width connected to one of said planar sections with a second apertured part of a corresponding type of retaining means having a width greater than said first width formed into the other planar section to provide a first level of closure retaining, and by the engagement of a first protruding part of a second type of retaining means having a predetermined width connected to one of said planar sections with a second apertured part of a corresponding type of retaining means having a width substantially the same as said predetermined width formed into the other planar section to provide a second level of closure retaining, and
(f) wherein said outer casing and said edge guard means are configured to foldably form a closed eight-sided container for interiorly retaining said sharps securely against at least one resilient pad.

7. The reopenable disposable sharps container of claim 6 having one resilient pad attached to an inner surface of a bottom section wherein said top section is transparent to permit visual inspection of said sharps contained therein.

8. The reopenable disposable sharps container of claim 6 wherein said top, bottom and hinged sections are integrally formed from a single blank of material and wherein said hinged section further comprises means for allowing variable spacing between said top and bottom sections when said container is in the folded closed position.

9. The reopenable disposable sharps container of claim 8 wherein said first protruding part comprises locking tab means integrally formed with said top section, and said second apertured part comprises slot means configured to frictionally receive said tab means.

10. The reopenable disposable sharps container of claim 6 further comprised of a pair of adhesive coated foam pads disposed therein for retaining the disposed sharps, and comprising:
an adhesive coating on said pair of foam pads disposed in a complementary pattern wherein the deposited sharps are adhesively retained to said pads while the mutual adherence of said pads by adhesive coating to adhesive coating contact is precluded.

* * * * *